United States Patent [19]

Goulay et al.

[11] Patent Number: 4,652,555

[45] Date of Patent: Mar. 24, 1987

[54] HEPARIN COMPOSITIONS FREED OF MINERAL SALTS, PARTICULARLY OXALATES, AND PROCESS FOR OBTAINING SAME

[75] Inventors: Jean Goulay, Oissel; Jean Choay, Paris; Jean-Pierre Duclos, Maromes, all of France

[73] Assignee: Choay S.A., Paris, France

[21] Appl. No.: 452,197

[22] Filed: Dec. 22, 1982

Related U.S. Application Data

[63] Continuation of Ser. No. 931,892, Aug. 8, 1978, abandoned, and a continuation of Ser. No. 63,838, Aug. 6, 1979, abandoned.

[30] Foreign Application Priority Data

Aug. 8, 1977 [GB] United Kingdom ............... 33170
Dec. 14, 1977 [GB] United Kingdom ............... 52047

[51] Int. Cl.$^4$ .................. A61K 31/725; C08B 37/10
[52] U.S. Cl. .................................... 514/56; 536/21
[58] Field of Search .................. 424/183; 536/21; 514/56

[56] References Cited

U.S. PATENT DOCUMENTS 3,135,660 6/1964 Bush et al. ............................ 536/21
3,482,014 12/1969 Koh ..................................... 424/183
4,168,377 9/1979 Choay et al. ........................ 424/183

Primary Examiner—Johnnie R. Brown
Attorney, Agent, or Firm—Weiser & Stapler

[57] ABSTRACT

This invention relates to oxalate-free preparations of heparin, particularly in the form of calcium salts of heparin, which can be used for the preparation of injectable solutions of heparin which have long storage life.

The invention is also directed to a process for freeing heparin from its oxalate content, such as by fractional precipitations by alcohol in the presence of adjusted amounts of mineral salt, until the heparin precipitated contains less than about 70 ppm of oxalate but may contain less than about 30 ppm, preferably even less than 20 ppm.

48 Claims, No Drawings

HEPARIN COMPOSITIONS FREED OF MINERAL SALTS, PARTICULARLY OXALATES, AND PROCESS FOR OBTAINING SAME

This application is a Continuation of two co-pending applications, both now abandoned, Ser. No. 931,892 filed on Aug. 8, 1978 entitled "Heparin Compositions Freed Of Mineral Salts Particularly Oxalates, And Process For Obtaining Them" in the name of Goulay, Choay and Duclos and Ser. No. 63,838 filed on Aug. 6, 1979 entitled "Heparin Compositions Freed Of Mineral Salts, Particularly Oxalates, And Process For Obtaining Them" in the name of Goulay, Choay and Duclos.

The invention relates to a process for the purification of heparin and heparin salts and to the heparin products obtainable by the process, the properties of which are improved compared to the previously known heparin salts.

Sodium salts of heparin (also called "sodium heparinates") are conventionally used for the production of injectable solutions of heparin. Mixed calcium-sodium heparinates or calcium-magnesium heparinates and advantageously calcium heparinates, have more recently been brought into use, in order to overcome a number of undesirable vascular reactions, particularly in the injection area, due to the sodium ions.

Mixed heparinates, i.e. calcium-sodium heparinates, calcium-magnesium heparinates, sodium-free heparinates, and particularly calcium heparinates are advantageously prepared from an initial heparinate, of sodium for example, by the process defined in British Pat. No. 1,471,482 corresponding to U.S. patent application Ser. No. 459,712, now U.S. Pat. No. 4,168,377. The process comprises contacting the initial simple salt or heparin in an aqueous medium with a salt of the desired metal to be substituted at least partially for the metal in the initial heparin salt, to form an intermediate mixed heparin salt containing the desired metal, and separating the so formed intermediate heparin salt from free metal ions contained in said medium. To the extent that a heparin salt further enriched with the metal of substitution is desired, the intermediate heparin salt referred to above can be recontacted in an aqueous medium with a salt of the desired metal. The conditions of operation of this process can be adjusted so as to obtain a simple heparinate of the substitution metal free of the metal contained in the initial heparin salt.

It has been found that on storage of solutions of heparin salts containing calcium ions, deposits or precipitates tend to form with the appearance of turbidity in the solutions. Obviously this tendency to the formation of precipitates or turbidity, which becomes greater as the said solutions are more concentrated in heparin, is of particular disadvantage in the case of injectable solutions of heparin intended for therapeutic use. Such solutions are prepared in advance industrially, notably in the form of predetermined doses, such a ampules or disposable syringes, such solutions must remain perfectly clear even after several months of storage. The formation of small deposits or even slight turbidity does of course render the solutions inappropriate for therapeutic administration. The necessity of using only clear solutions of heparin is apparent when it is considered that particles or crystals are no longer visible when their sizes are below approximately 50 microns and that capillary vessels in man have internal diameters as low as 1-3 microns. Moreover the presence, in injectable solutions of such particles or crystals even if no longer visible without optical equipment, may become particularly deleterious where the active principle injected is heparin, due to its anticoagulant properties. Thus the hemorrhagic risks induced by such solid particles injected in the patient may be increased by the otherwise desired essential activity of heparin.

The fact that a heparin solution remains limpid does not necessarily mean that no precipitate has formed. As a matter of fact it may happen, particularly in those instances where precipitation takes place very slowly, that the minute crystals (particularly sub-visible particles having sizes less than 50 microns) which form tend to coalesce into very few crystals or even into a single relatively sizable crystal which of course would not cause alteration of the overall limpidity of the solution. Consequently the injection of such a solution may be at least as harmful as in the preceding case.

All of the risks mentioned above are increased as the concentration of heparin in the standard pharmaceutical solutions increases although they may vary according to the type of injection (subcutaneous, intramuscular, intravenous, etc. . . . ). As is well known however, it is often desired to use heparin concentrations as high as possible in which case the potential for precipitation and the formation of sub-visible particles becomes a very serious problem.

In an attempt to overcome such difficulties, recourse is often had to storage of the freshly formed heparin solutions for extended periods before use. This practice is useful particularly for solutions of heparin salts of physiologically acceptable metals, composed at least in part of calcium, since any precipitates which forms on storage can be removed by filtration before the solutions are processed further, for instance of distribution into ampoules or dispensable syringes.

It will obviously be appreciated that the greater the pre-storage time, the less economical the production of the final pharmaceutical preparations.

The object of the invention is therefore to essentially overcome all of the difficulties referred to above. Therefore a particular object of the invention is to provide heparins of injectable quality usable for the preparation of solutions, particularly injectable solutions, having long storage-life.

Another object of the invention is to provide a process for obtaining such heparins, which obviate the need for prestorage of the type referred to.

It has in fact been found that most of the difficulties referred to above may be attributed to the presence in solutions of heparins of injectable quality, of various mineral salts, in quantities (up to 2.5% by weight). The nature of mineral depends upon the origin of the tested batch, the processes used for their extraction of heparin from natural sources. Another source of such mineral salts may be the processes used to decolorize or whiten the natural heparins obtained, to meet the standards of freedom from color normally required for heparins of injectable quality. This is possible though the content of mineral salts remains within limits tolerated by current regulations, for instance the standards of the French CODEX.

The greater part of the residual salts in heparin are constituted by chlorides and sulfates which may respectively amount up to 1%. Other salts, particularly carbonates, and sulfites, are present in smaller proportions.

The transformation of sodium salts of heparin into calcium containing salts of heparin, according to the process referred to above, for example, should reduce the proportions of these salts due to the lower solubility of the calcium sulfates, sulfites and carbonates. The latter should as a matter of fact be separable as solids from the clear solution of the calcium-containing salts of heparin.

It has been observed, however, that, most surprisingly after the transformation of sodium heparinate into calcium heparinate, particularly in accordance with the above mentioned process, the content of the above mentioned residual mineral salt is only slightly modified compared to that of the initial sodium heparinate.

Even more surprising was the finding that salts of heparin, including those which contain a metal formed at least in part of calcium, can be solubilized in form of limpid aqueous solutions, even though they may still contain minor, yet non-negligible amounts of oxalic ions. This was all the more unexpected as oxalates of metals like calcium are, as is well known, highly water-insoluble.

The reasons for this behaviour is not yet well understood. Nevertheless, a change in the normal solubility conditions of calcium oxalates has been ascertained, particularly when calcium chloride is in excess. Thus, it has been found that commercially available injectable heparins or heparinates may have residual salt-contents varying from 1.0 to 2.5% in weight, and from about 40 to 300 ppm oxalate ions, and sometimes even more.

It has been found that the elimination of the mineral salts, preferably of the traces of oxalates from the treated heparins results in the disappearing of turbidity and deposits which were liable to occur in the calcium heparinate solutions after the preparation of said solutions. It has been further found that upon long storage-time, no substantial increase of sub-visible particles (as detectable by conventional optical equipment, such as counters of particles liable of detecting particles having size ranging from 2 to 50 microns) is obtained in such solutions, provided their contents in oxalate ions is sufficiently reduced.

The calcium or mixed calcium, heparinate solutions which have undergone a purification process according to the invention as hereinafter disclosed, remain clear, even after having been stored for several months. No turbidity or deposit appears. Their contents in sub-visible particles are not increased upon long storage time, whereby the risks of crystals coalescence referred to hereabove is reduced too.

Heparins or heparin salts according to the invention are thus those, the content of which is residual mineral salts, particularly of oxalates, is sufficiently low for enabling the injectable solutions prepared starting from such heparins and more especially calcium heparinate solutions—under concentrations normally used for this type of administration, to remain perfectly clear, even after several months of storage such as at least six months.

Heparin salts, particularly calcium salt of heparin according to the invention, which contain less than about 70 ppm oxalate ions can be brought in the form of solutions, particularly injectable solutions, which remain clear, whose contents of sub-visible particles, if still any, remain substantially constant, upon protracted storage which can be as long as two years and even three to five years.

Although the most preferred heparin salts according to the invention are those which contain less than about 30 ppm or even less than about 20 ppm oxalate ions, those heparin salts which contain from about 30 to about 70 ppm meet nonetheless the above mentioned standards of clearness and long storage stability. Therefore, they also consist of preferred embodiments of the invention.

The aqueous solutions of calcium salt of heparin which contain above about 70 ppm of oxalates are subject to higher risks that precipitation or turbidity phenomena occur within the 6 month-period which follows their preparation.

Preferably they further have a content in residual mineral salts below 0.5% and preferably below 0.3%.

It must be understood that the expression "mineral salts" is not restricted to salts of mineral acids, such as sulfuric or hydrochloric acid, but also includes the salts of acids like oxalic or carbonic acid, or even of organic acids of low molecular weight, such as acetic acid.

It has been found that such heparin salts can be used for the production of injectable solutions which can be stored or shelved over prolonged periods of time, even when the metal of the heparin salts is, at least in part, one which, like calcium, forms oxalates which are not water-soluble.

The above mentioned storage is understood to be at room temperature, such as in the range of about 20°–25° C.

The invention also provides a process for obtaining purified heparins according to the invention, starting from commercially available products, inclusive of strongly discolored heparin products, as obtained by conventional discoloration methods, particularly oxidative methods which, as it has been found, are liable of increasing the oxalate of the so treated heparins.

The above mentioned "mineral salts" can be considered as non heparin salts.

The process according to the invention applicable to a starting heparin preparation to be purified or, more generally, a mixture of heparin and other salts, particularly mineral salts, brings into play a selective precipitation utilizing the difference of solubility between heparin salts and residual mineral salts. It comprises adding to an aqueous solution containing the heparin-mineral salts mixture an amount of a non-ionic precipitating agent such as alcohol, for instance ethanol, so adjusted as to cause a selective precipitation of the heparin or heparin salts while the mineral salts remain in the aqueous solution, recovering the heparin and, if need be, repeating this selective separation on a new aqueous solution of the heparin so recovered until the concentration of oxalate in the final heparin is less than a threshold which may be about 70 ppm in a number of cases, but is as low as 30 ppm, preferably even less than 20 ppm when long storage time (two years or even three to five years for instance) are required and when total security as regards non precipitation is required for that period.

It is even contemplated to obtain heparin having only traces of oxalate ions when detected by the presently available techniques.

According to a preferred embodiment of the process of the invention, the heparin used, is in the form of a salt of a metal, e.g. sodium, lithium, potassium, the oxalate of which are themselves water-soluble. Another metal particularly like calcium, of which the oxalates are water-insoluble, or possibly magnesium can be substituted, at least partially, for the metal of the purified heparin finally obtained, substantially freed from its oxalates.

The concentration of the heparin solution used for such treatment may vary widely. It is preferable, for practical reasons, that the solution should not be too dilute since the volume of ethanol used is proportional to that of the treated solution. For an equal quantity of heparin, the more dilute the solution, the larger the amount of ethanol required. On the other hand, the heparin solutions must not exceed a certain degree of concentration since their viscosity inreases rapidly, and the heparin precipitation, starting from these solutions, could possibly carry down a large amount of the initial impurities which are intended to be separated.

Taking these conditions into account, the process is advantageously carried out on solutions the concentration of which is of the order of that of the solutions usually used for injections, that is containing from about 40 to about 250 g/l of sodium heparinate (corresponding to about 5,000 to 30,000 IU/ml).

The pH of the solution influences the result of the purification. An acid solution aids in treating the mineral salts in the solution, particularly oxalates, and consequently improve the separation.

Besides, heparin may be affected by strong acids. A solution having pH above 3.5 and preferably between 5 and 7 is advantageously used.

A sufficient amount of ethanol is added to the heparin solution thus prepared, so that substantially all of the heparin precipitates while the mineral salts remain in the hydroalcoholic solution. For one volume of heparin solution, 0.5 to 1.5 volume of ethanol is preferably used.

Preferably a practically pure neutral alcohol (99 to 100° GL) is employed.

The heparin precipitate will be separated from the supernatant solution and then kneaded and washed in order to eliminate all remaining traces of solution. The washing is preferably done with absolute alcohol. The heparin is then recovered by filtration and dried.

If the first separation is incomplete, the treatment of the heparin precipitate may be repeated until heparin salts meeting the above indicated requirement are obtained.

Most of the initial heparin is recovered in the course of the above described precipitation; the rest remains in the hydroalcoholic solution. The latter may be treated with another quantity alcohol in order to obtain a new heparin precipitation.

The purification process of the invention has been found to be applicable in all instances for the removal of the free oxalates contained in commercial heparins, regardless of their sources.

However, while this process certainly enables the removal of any measurable free oxalates to provide heparins which contain less than 30 and even less than 20 ppm, thereof, when applied to a heparin salt of a metal, like sodium, of which the corresponding oxalate is water-soluble, it has occured in a few instances that upon converting at least partially such heparin salt into one of a metal, like calcium, of which the oxalates are insoluble, the resulting product was finally found to contain greater amounts of free oxalates.

Although no scientific explanation can be offered at present for this phenomena, it is assumed that part of the oxalates contained in the commercial heparins from some sources behaves as if it were absorbed or fixed on the heparin molecules, the latter then behaving, apparently, as an anion-exchanger. Therefore, as a result of this phenomena, the final heparin salts may not be suitable for the production of injectable solutions of the heparin can be stored over prolonged periods of time.

It has however been found further that this difficulty can be overcome by employing a further improved process of this invention which comprises contacting said non-ionic heparin-precipitating-agent in the above described purification process steps with an initial aqueous solution of the heparin to be purified (or of the heparin-mineral salt mixture) which contains water-soluble mineral salts other than oxalates in a concentration sufficient to favor a separation of the oxalates, including the apparently initially fixed or adsorbed oxalates which are then freed and remain in the aqueous solution upon the attendant precipitaton of the heparin salts.

Thus some of the other salts present in the heparin soluton to be purified may even, upon proper adjustment of their own concentration in the solution, whenever appropriate, participate in a more complete extraction of the oxalate ions.

Thus in preferred embodiments of the process according to the invention it will be usualy required to first adjust the concentration of said water-soluble mineral salts in the initial aqueous solution of heparin, prior to contacting the latter with the non-ionic heparin precipitating agent.

As matter of fact, it has been found that a sufficient concentration, particularly of salts comprising divalent anions and preferably too, monovalent anions, appears to cause the displacement of the oxalates possibly adsorbed on or fixed to the heparin.

If necessary it is appropriate to repeat the precipitation steps upon recontacting a solution of the heparin so recovered and of water-soluble mineral salts other than oxalates in an adjusted concentration as hereabove defined until the concentration of total oxalates in the final heparin is less than 30 ppm, preferably even less than 20 ppm.

Preferably, the metal (or metals) of the salts having divalent anions, other than oxalates, contained in or possibly added to the initial heparin solutions is selected from those containing metals the oxalates of which are water-soluble. Carbonates are particularly sodium carbonate, have been found most effective in the process according to the invention.

Preferably too the heparin in the above said solution is in the form of a heparin salt of the same metal as that of the mineral salts. Any possibility of exchange of the metal contained in the latter mineral salt for the metal of the heparin salt is then avoided whereby the metal content of the purified heparin salts is kept under close control.

Advantageously the concentration of the mineral salts in the solution to be contacted with the non ionic precipitating agent such as alcohol, is adjusted to a value from 0.3 to 2.5, for instance of about 0.5% by weight of the heparin.

Advantageously too the starting solution also contains salts having monovalent anions of at least one metal, the oxalate of which is water-soluble. Sodium chloride is representative of such salts. In a preferred embodiment of the process according to the invention, the concentration of monovalent salt has, or is adjusted to have a value ranging from 1 to 7%, for instance of about 2.5% by weight/volume of solution.

It has been found advantageous, though not necessary, that the pH of the solution contacted with the non-ionic precipitating agent be between 7 and 10, for instance of the order of 8.5. This is actually the pH which is spontaneously established when the salt having divalent anions is sodium carbonate.

These salts having divalent and/or monovalent anions can then be easily eliminated in the final stage of the process, for instance in a final contacting step of the heparin solution with the non-ionic agent. Advantageously the pH is then adjusted for instance with hydrochloric acid, to a slightly acid value, sufficient for destroying the carbonates, particularly at a pH ranging from 3 to 7. The chloride ions remain in the aqueous solution, when the final heparin salt is precipitated.

Heparin compositions, particularly heparin salts are thus obtained which are substantially oxalate-free and which are either:

(a) directly suitable for the preparation of pharmaceutical compositions, particularly injectable or perfusable solutions having long storage life, even when the metallic cations of the heparin salts are at least in part those of metals or the oxalates or which are highly insoluble, like calcium, (b) suitable as starting heparin salts from which the metallic cations contained therein can be substituted at least in part advantageously, though not necessarily, according to the process of British Pat. No. 1,471,482 already mentioned hereabove, to provide other substantially oxalate-free heparin salts which are then formed into pharmaceutical composition having long storage life.

The invention thus concerns more particularly among the oxalate-free heparin preparations, the metallic salts of heparin, i.e. either simple salts of heparin, such as the sodium, potassium, calcium or magnesium salts of heparin, or mixed salts of heparin containing at least two of the metallic cations in any relative proportions, all of these heparin salts being substantially free of oxalates in that they contain less than a threshold of about 70 ppm in a number of cases, particularly from about 30 to about 70 ppm, even though most preferred heparin preparations may contain as low as 30, preferably less than 20 ppm of total oxalates (hereafter termed as oxalate-free heparins). Among the mixed salts one may cite the preferred series of those which contain sodium and calcium.

The invention also concerns pharmaceutical preparations in which the oxalate-free heparin is associated with pharmaceutical vehicle, more particularly the oxalate-free, preferably colorless heparin preparations having an activity of at least 120, preferably above 150 International Units (IU)/mg, free of pyrogens, as well as the highly concentrated solutions of heparin useful for their application in therapy for the control of blood-coagulation, particularly oxalate-free, preferably colorless, solutions suitable for subcutaneous injection containing from 5000 to 35,000 IU/ml of heparin, preferably from 20,000 to 30,000, such as 25,000 IU/ml, or oxalate-free solutions suitable for intravenous injection, containing from 1,000 to 10,000, for instance 5,000 IU/ml of heparin, etc.

Advantageously the heparin of said preparation is in the form of a physiologically acceptable metal salt of heparin containing one or several metal cations. Preferably the metal is at least in part calcium. Advantageously calcium is the only metal of said heparin salt. The pharmaceutical preparations may be advantageously presented in dispensable syringes, ready for use at the appropriate time.

The invention also concerns a method for controlling blood coagulation in man, which method comprises administering to him an effective dose of the oxalate-free heparin of the invention, such as from 13,500 to 50,000 i.u. by the subcutaneous route, twice a day, as required by the thrombotic state of the patient, or from 20,000 to 50,000 i.u. per 24 hours by the intra-venous route, evenly distributed over the day, advantageously by adjusted perfusions or of 5,000 to 10,000 i.u., three times a week, by the intramuscular route.

The purified heparin according to the invention may be used directly to prepare, e.g. injectable solutions of usual dosages and concentrations. Alternately, the purified heparin also may be used as a starting material for preparing other salts, such as calcium heparinates or mixed calcium-magnesium, calcium-sodium salts, for instance, according to the process described in British Pat. No. 1,471,482.

FIRST EXAMPLE OF A PREFERRED PURIFICATION PROCEDURE OF HEPARIN

In a preferred alcoholic fractionating purification process of injectable sodium heparinate, sodium heparin of bovine or porcine origin, of injectable quality is used.

This heparinate is dissolved in demineralized water (having a resistivity from 300,000 to 800,000 $\Omega$/cm, preferably 500,000 $\Omega$/cm.

The concentration of the heparinate solution is settled between 5,000 and 30,000 IU/ml, preferably 25,000 IU/ml. 0.3% metacresol is added in order to prevent any contamination. The pH of the solution is maintained between 5 and 7, preferably 6.5, by adding either a reagent grade 5 N sodic solution, or a reagent grade 5 N hydrochloric acid solution. The solution conductivity remains between 7,000 and 15,000 $\mu$Mhos-cm.

0.7 volume of neutral ethyl alcohol (99° to 100° GL) s added to te heparinate solution thus prepared. One leaves the precipitate to settle and possibly adds a small amount of sodium chloride if necessary.

The precipitate is separated from the supernatant. It is once more solubilized in demineralized water, having the above described characteristics, so as to obtain a concentration roundabout 12,500 IU/ml. The pH is controlled to 5.5 if need be, having recourse to a NaOH 5 N or HCL 5 N solution. The solution is filtrated on a Millipore 0.3 filter. 1.2 volume of neutral ethyl alcohol (99°–100° GL) for 1 volume of solution is added under stirring. One leaves the precipitate to settle, possibly with addition of a small amount of sodium chloride.

The so obtained heparin precipitate is dehydrated by crushing in absolute ethyl alcohol, then filtrated under vacuum upon industrial Buchner, washed with absolute alcohol and dried under 1 torr vacuum at a temperature of 35°/40° C.

When further precipitations are needed, they are carried out in the same way as for the second precipitation step; i.e. heparin concentration of 12,500 IU/ml, pH 5.5, and 1.2 volume of absolute alcohol per 1 volume solution.

SECOND EXAMPLE OF A GENERAL PREFERRED PROCEDURE

First alcoholic fractionation

A sodium salt of heparin of injectable quality, of bovine or porcine origin is dissolved in demineralized water having a resistivity ranging from 300,000 to 800,000 ohms, and preferably of 500,000 ohms, to provide a solution having a heparin concentration of from 5,000 to 30,000 IU/ml and preferably 25,000 IU/ml.

Metaeresol is added in an amount to provide a 3/1000 concentration. The pH of the solution is adjusted to a value from 7 to 10; preferably 8.5 by addition of a sodium carbonate solution (anhydrous sodium carbonate) in a proportion of 0.5% relative to the initial heparin weight.

The conductivity of the solution ranges then from 7,000 to 15,000 μ Mhos/cm. Sodium chloride crystals are then added to the solution in a proportion of 2.5% weight/volume. 0.7 volume of neutral ethyl alcohol titrating 99° to 100° G.L. (Gay-Lussac degrees) is then added, under stirring, to the volume of the heparin solution. The heparin precipitate is then collected, after 6 hours of standing of the medium.

Second alcoholic fractionation

The heparin precipitate thus obtained in redissolved in demineralized water having the above mentioned characteristics so as to obtain a concentration close to 12,500 IU/ml. The pH approximates then 8.5. Crystals of sodium chloride are then added in a 2.5% weight/volume proportion relative to the solution. One volume of neutral ethyl alcohol titrating from 99° to 100° G.L. is added under stirring.

The medium is left standing for 12 hours. The new heparin precipitate is collected.

The "second alcoholic fractionation" is repeated three times in the same conditions as above, thus providing 4 fractionating steps. The precipitate originating from the 4th alcoholic fractionation is redissolved in demineralized water having the previously mentioned characteristics, so as to obtain a concentration approximating 12,500 IU/ml. The pH is adjusted to 3 with hydrochloric acid, under vigorous stirring. Stirring is then maintained for another 15 minutes. The pH is then adjusted to 5.5 with 5 N sodium hydroxide. Sodium chloride cyrstals are added thereto in an amount of 2.5% weight/volume and the solution thus obtained is filtrated on a MILIPORE 0.3 μ membrane. 1 volume/volume of neutral ethyl alcohol titrating 99° to 100° G.L. is added to the filtrate under stirring.

The medium is left standing for 12 hours.

The obtained heparin precipitate is dehydrated by crushing in absolute ethyl alcohol and filtrated under vacuum. It is finally washed in absolute alcohol and dried under a 1 Torr vacuum at a temperature of 35°/40° C. An injectable sodium salt of heparin is thus obtained in which the proportion of total mineral salts is less than 0.5% and the total oxalate contents is below or equals at most 20 ppm. EXAMPLE I In this example, commercially available sodium heparinate titrating 160 IU/mg is used.

The total mineral salts content is 2.5% and the oxalate content is of the order of 220 ppm (i.e. 0.22%).

10,000 g of this heparinate are dissolved in a 300 liter steel-inox reactor by adding 50 l of demineralized water of a 500,000 μ/cm resistivity, previously filtrated on a Millipore membrane 0.22 μ.

The dissolution is achieved after one hour agitation. The pH is measured and adjusted at 6.5 by addition of NaOH 5 N or HCl 5 N. The volume is brought up to 64 l by means of the same demineralized water. The conductivity measured is 15,000 μMhos/cm. The temperature is kept between 15° and 30° C.

192 ml of newly distilled metacresol are added and 0.7 volume of a neutral ethyl alcohol (99°/100° GL) is added for 1 volume of the initial solution, that is 44.8 liters. The solution is left until a precipitate appears; if need be, a small amount of sodium chloride is added. The supernatant and the sodium heparinate precipitate are separately recovered; the mineral salt contents of the latter is below 0.5%, yet, about 200 ppm oxalate ions are still to be found therein.

The sodium heparinate is again solubilized in 50 liters of the same demineralized water of a 500,000 Ω/cm conductivity. If need be, the pH is adjusted to 5.5 by addition of NaOH 5 N or HCl 5 N. The measured conductivity is 15,000 μ Mhos-cm. The volume is brought up to 128 liters with the same demineralized water, 384 g of newly distilled metacresol are added and the whole preparation is left for 24 hours at room temperature. The heparin solution is filtrated on a 0.3 μ CWSS Millipore filter. The filtrate is recoverd. 30 liters of neutral ethyl alcohol (99°/100° GL) i.e. 1.2 volume, are slowly added under stirring to 25 l. of the filtrate. The product is then left until a precipitate appears. If need be, a small amount of sodium chloride is added.

The supernatant and the sodium heparinate precipitate are separately recovered. The latter is then dehydrated with absolute alcohol, crushed and filtrated under industrial vacuum on a Buchner funnel and finally dried and lyophilized. 9,400 g of sodium heparinate are thus obtained, that is a yield of 94%. This heparinate titrates 160 IU/mg. Its content in mineral salts is 0.15% including 30 ppm oxalate ions.

In order to recover the heparinate which is still retained in the hydro-alcoholic supernatants, the treatment is prolonged as follows:

There is added, under stirring, one volume of neutral ethyl alcohol (99°/100° GL) to one volume of supernatant of the first alcoholic precipitation. After 24 hours settling the clear to slightly opalescent supernatant is transferred and directed towards residual alcohols.

The precipitate is separated and recovered in absolute ethyl alcohol, dehydrated, crushed and dried.

Neutral ethyl alcohol (90°/100° GL) is added under stirring to the supernatant of the second preparation, in a proportion of 0.5 volume to one volume of supernatant, and then left to settle for 24 hours.

Sodium heparinate is recovered in conditions similar to those described in the case of the first supernatant.

The sodium heparinate thus obtained is used in the preparation of the calcium salt.

This preparation is effected according to the method described in the British Pat. No. 1,471,482.

To sum it up the treatment comprises: adding calcium chloride to a sodium heparinate solution so as to obtain a calcium enriched heparinate, then eliminating the freed sodium ions and re-adding calcium ions so as to obtain a calcium-ions-enriched heparinate.

By said process, a calcium salt of heparin is obtained, titrating 160 IU/mg, 10.3% calcium, 0.2% sodium, and 20 ppm oxalate ions.

EXAMPLE 2

A sodium heparinate prepared as in example 1, titrating 160 IU/mg and having a content of about 30 ppm oxalate is processed as described in the British Pat. No. 1,471,482 for the preparation of a calcium-sodium heparinate. In this example, calcium chloride is added only once to a sodium heparinate solution; freed sodium ions are then eliminated.

There has been thus prepared a calcium heparinate titrating 160 IU/mg and having a calcium content of about 7%. The content of oxalate ions of this heparinate salt is 18 ppm.

A solution of this calcium-sodium heparinate, titrating 25,000 IU/ml, stored in ampullae for several months exhibits no trace of precipitate.

EXAMPLE 3

The test carried out in example 2 has been repeated, this time completely transforming the sodium heparinate into calcium heparinate, according to the process described in the British Pat. No. 1,471,482.

The calcium heparinate thus obtained titrates 160 IU/mg, has a calcium content of about 10.5% and a sodium content below 0.1%. The content in mineral salts is 0.4%, including 20 ppm oxalate ions and the solutions so prepared, titrating 25,000 IU/ml, exhibits the same characteristics as the one of example 2, as concerns it storage capacity.

EXAMPLE 4

A commercial injectable sodium salt of heparin titrating 160 IU/mg as such is used in this example.

It mineral salts contents is of 2.5% and its oxalate contents is of 1,000 ppm (that is 0.1%). 10,000 g of this heparin are dissolved in 50 liters demineralized water having a 500,000 ohms resistivity, which had been previously filtrated on a 0.22 $\mu$ MILLIPORE membrane in a 300 liter stainless steel reactor.

The solution is left under stirring for 15 minutes and the volume is brought up to 64 liters by addition of demineralized water. The concentration is 25,000 IU/ml. 192 ml of freshly distilled metacresol, then 50 g of sodium carbonate in the form of an aqueous solution, and finally 1,600 g of sodium chloride crystals are added thereto. The solution is again left under stirring for 15 minutes. The pH, which should be of 8.5 is verified and, if needed, adjusted to 8.5 with a sodium carbonate solution 44 liters of natural ethyl alcohol titrating from 99° to 100° G.L. are added thereto, under stirring (0.7 volume of alcohol per one initial volume of the solution). The medium is left standing for 6 hours and the heparin precipitate is collected.

This heparin precipitate is then subjected to a second alcoholic fractionation after having been redissolved in 110 liters of demineralized water having the previously mentioned characteristics, to obtain a concentration approximating 12,500 IU/ml. The solution is left under stirring for 15 minutes and demineralized water is added up to a volume of 128 liters. 384 ml of freshly distilled metacresol are added. The pH is adjusted to 8.5 with a solution of sodium carbonate. 3,200 g. of sodium chloride are added. The solution is then left under stirring for 15 minutes. Neutral ethyl alcohol titrating from 99° to 100° G.L. is added in a proportion of 1 volume per volume of heparin solution, under stirring. The medium obtained is left standing for 12 hours. The heparin precipitate formed is recovered, after the removal of the supernatant.

The alcoholic fractionation is repeated three times again in the same conditions as in the second fractionation, on the heparin precipitate which is recovered each time from the preceding fractionation step.

The final heparin precipitate is then redissolved in demineralized water so as to obtain a concentration approximating 12,500 IU/ml, that is a solution having a volume of 128 liters. The pH is adjusted to 3 under vigorous stirring with hydrochloric acid. The solution is left under stirring for 15 minutes. The pH is adjusted to 5.5 with 5 N. sodium hydroxide. 384 ml of freshly distilled metacresol and then 3,200 g of sodium chloride crystals are added. The obtained solution is filtrated on a 0.3 u MILLIPORE membrane. All these operations are carried out at a temperature ranging from 15° to 30° C. 1 volume of neutral ethyl alcohol tirating from 99° to 100° G.L. is added to the filtrate under stirring. The solution is left standing for 12 hours.

The final heparin precipitate thus obtained is dehydrated by crushing in absolute ethyl alcohol, filtrated under vacuum and subjected to repeated washings with absolute alcohol and then dried under 1 Torr vacuum at a temperature of 35°/40° C. for 24 hours. The powder is crushed and again dried under a 1 Torr vacuum for 24 hours at a temperature of 40° C., so as to eliminate the ultimate traces of solvent. 9,100 g. of a sodium salt of heparin are obtained, whose contents in mineral salts are less than 0.5%, and in oxalate less than 20 ppm. The obtained yield on the fraction is 90.43%. The recovered titration IU/mg is: 157.

EXAMPLE 5

Other batches of calcium salt of heparin containing from about 40 to about 60 ppm of oxalates and aqueous solutions thereof containing 25,000 IU/ml were prepared. After storage for over more than one year neither any turbidity nor the formation of one or more crystals having sizes from 2 to 40 microns were observed.

The dosages of the oxalate ions in the purified heparins were effected after extractions by the method of J. R. HELBERT and M. A. MARINI, Biochem. J. (1963) 2 (5) pp. 1101–6, however modified in that the oxalate ions present in said heparins were extracted therefrom in the presence of an excess of sodium carbonate, prior to being adsorbed on a IRA 400 anionic resin, the use of which has been recommended by the authors. After their elution from the resin, the oxalate ions were dosed according to the fluorometric method of P. M. ZAREMBSKI and A. HODGKINSON, Biochem. J. (1965) 96,5,717–721).

We claim:

1. A metal salt of heparin, at least a part of which is calcium, which heparin contains less than about 70 ppm of oxalates.

2. The metal salt of heparin of claim 1, which contains from about 30 to about 70 ppm of oxalates.

3. The metal salt of heparin of claim 2, which contains less than about 30 ppm of oxalates.

4. The metal salt of heparin of claim 1, which contains less than about 0.5% of mineral salts.

5. The metal salt of heparin of claim 4, which contains less than about 0.3% of mineral salts.

6. A solution of a metal salt of heparin of claim 1, at least a part of which is calcium, which heparin contains less than about 70 ppm of oxalates and said solution having an activity of at least 120 IU/mg.

7. The solution of claim 6, wherein the solution has an activity of about 150 IU/mg.

8. The solution of claim 7, which is an injectable solution.

9. The solution of claim 8 which contains at least 1000 IU/ml. of heparin.

10. The solution of claim 9 which contains from about 5,000 to about 35,000 IU/ml. of heparin.

11. The solution of claim 10 which contains from about 20,000 to about 30,000 IU/ml. of heparin.

12. The solution of claim 10 which contains from about 1000 to about 10,000 IU/ml. of heparin.

13. The solution of claim 12 which contains about 5,000 IU/ml. of heparin.

14. An improved pharmaceutical composition useful for controlling blood coagulation in a man which comprises a limpid aqueous heparin salt solution containing heparin in an amount effective to control blood coagulation, which salt solution is of a physiological acceptable metal and at least part of the metal being calcium, wherein the oxalate content of the salt is less than about 70 ppm.

15. The composition of claim 14 wherein the oxalate content of the salt is less than about 30 ppm.

16. The composition of claim 14 wherein the solution is of a metal which is substantially all calcium.

17. The composition of claim 16 wherein the solution is substantially sodium-free.

18. The composition of claim 14 wherein the solution is an injectable solution.

19. The composition of claim 14 wherein the solution is of mixed salt of sodium and calcium.

20. The composition of claim 14 wherein the heparin content if from about 5,000 to 35,000 IU/ml.

21. The composition of claim 1 wherein the heparin salt solution is virtually colorless.

22. The composition of claim 17 wherein the solution is virtually free of visible sub-visible oxalate salt particles.

23. The heparin salt solution of claim 6 which remains free of turbidity or deposits of oxalate salts upon storage at room temperature for a period of at least six months.

24. A method for controlling blood coagulation in man which comprises administering an effective dosage to control coagulation of a heparin of any one of claims 1, 2, 3, 4, 5, 6, 7, 9, 10, or 13.

25. A process for converting a starting heparin salt of a metal, the oxalates of which are water-soluble, and which contains mineral salts including water-soluble oxalate, into a salt of heparin at least part of which is calcium and which heparin salt contains not more than about 70 ppm of oxalate, which comprises:
mixing a non-ionic precipitating agent with an aqueous solution of the heparin salt, the amount of precipitating agent causing selective precipitation of the heparin salt from said solution while leaving mineral salts including oxalate in solution, recovering the precipitated salt of heparin and repeating said mixing and precipitation steps until a purified heparin salt containing no more than about 70 ppm of oxalate is obtained.

26. The process of claim 25 which comprises contacting the purified heparin salt with a calcium salt and thereby substituting calcium for at least a part of the metal of said starting heparin salt.

27. The process of claim 25 which comprises repeating said mixing and precipitation steps until a purified heparin salt containing no more than about 30 ppm of oxalate are present.

28. The process of claim 27 which comprises contacting the purified heparin salt with a calcium salt and thereby substituting calcium for at least a part of the metal of said starting heparin salt.

29. The process of claim 25 wherein the heparin mineral salt solution contains from about 40 to 250 g/l of sodium heparinate.

30. The process of claim 25 wherein the heparin mineral salt solution contains from about 5,000 to about 30,000 IU/ml. of heparin.

31. The process of claim 25 wherein the pH of the solution is adjusted between 7 and 10.

32. The process of claim 25 wherein the precipitation is effected using from about 0.5 to 1.5 volume of the non-ionic precipitating agent.

33. The process of claim 25 which comprises prior to the mixing of the non-ionic precipitating agent, adjusting the concentration of mineral salts other than oxalate to a proportion sufficient to favor the separation of the oxalate.

34. The process of claim 25 wherein the heparin mineral salt solution contains at least one salt having a divalent anion of a metal, the oxalate of which is water soluble.

35. The process of claim 33 wherein said divalent salt is a carbonate.

36. The process of claims 25 or 33 wherein the concentration of salts having divalent anions other than the oxalate in said solution, ranges from about 0.3% to about 2.5% by weight of the heparin content of said solution.

37. The process of claim 33 wherein the concentration of salts having divalent anions other than the oxalates in said solution, ranges from about 0.3 to about 2.5% by weight of the heparin content by said solution.

38. The process of claim 36 wherein said salts also comprise at least one salt having an anion of a metal of the oxalate which is water soluble.

39. The process of claim 37 wherein said salt having a monovalent anion is a chloride.

40. The process of claim 25 wherein the heparin in the solution to be contacted with the non-ionic agent is a sodium salt of heparin.

41. The process of claim 25 wherein the heparin is in the form of a salt of the same metal as the metal of said mineral salts.

42. The process of claim 25 which comprises further substituting at least in part the metal in the heparin salt obtained from said process with a metal, the oxalate salt of which is water insoluble.

43. The process of claim 25 wherein said non-ionic precipitating agent is an alcohol.

44. The process of claim 43 wherein said alcohol is ethanol.

45. The process of claim 25 further comprising repeating the selective separation on an aqueous solution of the heparin so-recovered.

46. The process of claim 45 which is repeated until the oxalate content of the heparin is not more than about 30 ppm.

47. The process of claim 46 wherein said pH is in the range from about 5 to about 7.

48. A process of selective precipitation for converting heparin which contains heparin mineral salts including oxalate mineral salts to a salt of heparin, at least part of which is calcium heparin and which heparin calcium contains not more than about 70 ppm of oxalate which comprises:
(1) mixing a non-ionic precipitating agent with an aqueous solution of the heparin mineral salt,
(2) selectively precipitating the heparin salts from the solution while leaving the mineral salts, including the oxalates in solution, the amount of precipitating agent being such as to cause selective precipitation of the heparin, and
(3) recovering a purified calcium heparin salt containing no more than about 70 ppm of oxalate.

* * * * *